(12) United States Patent
Burns (10) Patent No.: US 11,761,942 B2
(45) Date of Patent: Sep. 19, 2023

(54) SYSTEM AND METHOD FOR ENVIRONMENTAL SAMPLING AND ANALYSIS

(71) Applicant: Terracon Consultants, Inc., Olathe, KS (US)

(72) Inventor: Perre E. Burns, Lebanon, IN (US)

(73) Assignee: Terracon Consultants, Inc., Olathe, KS (US)

( * ) Notice: Subject to any disclaimer, the term of this patent is extended or adjusted under 35 U.S.C. 154(b) by 0 days.

(21) Appl. No.: 17/523,405

(22) Filed: Nov. 10, 2021

(65) Prior Publication Data

US 2022/0178903 A1     Jun. 9, 2022

Related U.S. Application Data

(60) Provisional application No. 63/112,238, filed on Nov. 11, 2020.

(51) Int. Cl.

| | |
|---|---|
| *G01N 33/24* | (2006.01) |
| *E21B 49/02* | (2006.01) |
| *G01N 1/08* | (2006.01) |
| *G01N 1/10* | (2006.01) |
| *G01N 1/22* | (2006.01) |
| *E02D 1/02* | (2006.01) |
| *E21B 49/08* | (2006.01) |
| *G01N 35/00* | (2006.01) |

(52) U.S. Cl.
CPC ............. *G01N 33/24* (2013.01); *E02D 1/025* (2013.01); *E02D 1/027* (2013.01); *E21B 49/02* (2013.01); *E21B 49/08* (2013.01); *G01N 1/08* (2013.01); *G01N 1/10* (2013.01); *G01N 1/2294* (2013.01); *G01N 35/00871* (2013.01)

(58) Field of Classification Search
CPC ............ G01N 33/24; G01N 1/08; G01N 1/10; G01N 1/2294; G01N 35/00871; E02D 1/025; E02D 1/027; E21B 49/02; E21B 49/08
See application file for complete search history.

(56) References Cited

U.S. PATENT DOCUMENTS

| | | | | |
|---|---|---|---|---|
| 2,613,916 A | * | 10/1952 | Gregory | E21B 27/00 |
| | | | | 175/309 |
| 2,922,103 A | * | 1/1960 | Smith | E21B 49/005 |
| | | | | 324/324 |
| 3,690,166 A | | 9/1972 | Grice | |
| 3,872,935 A | * | 3/1975 | Mielke | E21B 7/26 |
| | | | | 175/58 |
| 5,010,776 A | | 4/1991 | Lucero et al. | |

(Continued)

FOREIGN PATENT DOCUMENTS

| | | | | |
|---|---|---|---|---|
| CN | 100489871 C | * | 5/2009 | E02D 1/02 |
| CN | 109696324 A | * | 4/2019 | G01N 1/08 |

(Continued)

*Primary Examiner* — Ryan D Walsh
(74) *Attorney, Agent, or Firm* — Stinson LLP (57) ABSTRACT

A system and method for environmental sampling and analysis system are described. The system and method provide for concurrent collection and sampling of subsurface materials and sensing of one or more subsurface environmental conditions. In particular, the system and method provide for high resolution environmental site characterization.

40 Claims, 8 Drawing Sheets

FIG. 1

(56) References Cited

U.S. PATENT DOCUMENTS

| | | | |
|---|---|---|---|
| 5,128,882 A * | 7/1992 | Cooper | G01V 8/02 |
| | | | 356/73 |
| 5,435,176 A * | 7/1995 | Manchak, III | E21B 10/32 |
| | | | 175/21 |
| 5,488,876 A | 2/1996 | Casey et al. | |
| 5,497,091 A * | 3/1996 | Bratton | G01V 3/02 |
| | | | 324/438 |
| 5,589,825 A | 12/1996 | Pomerleau | |
| 6,035,950 A | 3/2000 | Heller et al. | |
| 6,487,920 B1 | 12/2002 | Robbat, Jr. | |
| 7,221,171 B2 | 5/2007 | Sohl, III et al. | |
| 10,208,585 B2 * | 2/2019 | Surowinski | E21B 47/047 |
| 10,371,637 B1 * | 8/2019 | Jaster | G01V 8/10 |
| 2002/0194937 A1 * | 12/2002 | Scott | E02D 1/04 |
| | | | 175/2 |
| 2004/0074639 A1 | 4/2004 | Runia | |
| 2006/0158652 A1 * | 7/2006 | Rooney | G01N 21/251 |
| | | | 356/406 |
| 2009/0107725 A1 | 4/2009 | Christy et al. | |
| 2012/0060630 A1 | 3/2012 | Van Straaten et al. | |
| 2013/0263680 A1 * | 10/2013 | Barere | G01N 1/44 |
| | | | 73/863.12 |
| 2014/0231322 A1 | 8/2014 | Bastiaens et al. | |
| 2018/0267010 A1 * | 9/2018 | Ellson | E21B 49/08 |

FOREIGN PATENT DOCUMENTS

| | | | | |
|---|---|---|---|---|
| CN | 114002407 A * | 2/2022 | | |
| DE | 4429136 A1 * | 3/1995 | | E21B 33/127 |
| KR | 20090010819 A * | 1/2009 | | |
| KR | 101064447 B1 * | 9/2011 | | |

\* cited by examiner

SYSTEM AND METHOD FOR ENVIRONMENTAL SAMPLING AND ANALYSIS

CROSS-REFERENCE TO RELATED APPLICATION

This application claims priority to U.S. Provisional Application No. 63/112,238, filed on Nov. 11, 2020, the entirety of which is hereby incorporated by reference.

FIELD

The present disclosure relates to a system and method for environmental sampling and analysis. The system and method provide for the concurrent collection and sampling of subsurface materials and sensing of one or more subsurface environmental conditions. In particular, the system and method provide for high resolution environmental site characterization.

BACKGROUND

Subsurface investigations are performed to assess various environmental, geological, and/or geotechnical conditions at a site. For example, subsurface investigations are conducted at sites with suspected contamination of chemicals or materials that may pose an environmental risk or hazard. Samples of subsurface materials are collected and analyzed with the goal of characterizing the site and determining further actions that may be required to make the site suitable for development, prevent groundwater contamination and/or comply with applicable rules and regulations.

Sampling of subsurface materials, particularly soil, groundwater and other subsurface materials, is conventionally performed by driving a sampling device having a hollow tube into the subsurface. A core sample of subsurface material is collected in the hollow tube as the sampling device is driven deeper into the subsurface. Subsequently, the sampling device is withdrawn from the borehole and the sample is removed from the hollow tube. The sampling device can be driven into the subsurface using various drilling techniques.

An especially convenient drilling technique includes direct push technology where a sampling device or probe are driven into the subsurface using a hydraulic hammer. Unlike rotary drilling techniques, cuttings of subsurface materials are not generated using direct push technology. Thus, direct push technology advantageously provides for efficient subsurface sampling that disturbs less of the subsurface and produces less potentially contaminated material that must be disposed of or removed from the sampling site. Also, rigs designed for direct push are typically more compact and portable than rotary drilling rigs. As such, direct push technology advantageously provides for efficient subsurface sampling in locations that would not be suitable or accessible to larger rotary drilling rigs.

Despite the advantages of direct push technology, site characterization remains at relatively low resolutions where only a small amount of subsurface data is obtained. Samples of subsurface materials that are obtained from the sampling device can be qualitatively screened in the field (e.g., analyzed for relative volatile organic compound (VOC) content using a photoionization detector (PID)) and/or quantitatively analyzed by collecting, preserving, and submitting the samples to an analytical laboratory. However, the sampling device must be removed from the subsurface at intervals in order to collect and screen samples. Further, no information regarding the subsurface samples is obtained until after the sampling device is driven to the desired depth in the subsurface and withdrawn from the borehole, and the subsurface samples are collected and analyzed. Thus, subsurface investigations using conventional direct push technology remains an iterative, time-consuming process where typically only a small amount of subsurface data is collected.

Direct push probing tools have been developed. These tools include sensors that measure subsurface conditions. For example, a membrane interface probe measures the relative concentration of VOCs in the subsurface. Although these tools are useful for screening and logging subsurface conditions, these tools do not permit the concurrent sampling of subsurface materials. Instead, a second borehole must be made to advance a sampling device. This process increases the time and cost necessary to conduct the subsurface investigation. Thus, there remains a need for efficient and cost-effective systems and methods that can provide for high resolution site characterization.

BRIEF SUMMARY

Aspects of the present disclosure relate to an environmental sampling and analysis system. In various embodiments, the system comprises an outer housing and an inner housing at least partially disposed in the outer housing. The inner housing defines an interior sized and shaped to receive a sample collection liner. The sample collection liner is configured to receive a sample of a subsurface material. The inner and outer housings are configured to be driven into a subsurface to obtain the sample of the subsurface material. A passageway is defined by at least one of the outer housing or the inner housing. The system further includes at least one of a sensor or a fluid port. The sensor is supported by the outer housing. The sensor is configured to detect at least one condition of the subsurface located outside of the outer housing when the inner and outer housings are driven into the subsurface and the sample of a subsurface material is collected. The fluid port is positioned in the outer housing. The fluid port is configured to permit the withdrawal of a subsurface fluid and/or injection of a fluid to the subsurface when the inner and outer housings are driven into the subsurface.

Additional aspects of the present disclosure relate to a method for environmental sampling and analysis. In various embodiments, the method comprises driving an environmental sampling and analysis system comprising a sensor configured to detect at least one condition of the subsurface located outside of the system when the system is driven into the subsurface; collecting a sample of a subsurface material in the environmental sampling and analysis system as the system is driven into the subsurface; and detecting at least one condition of the subsurface with a sensor in the environmental sampling and analysis system.

Other objects and features will be in part apparent and in part pointed out hereinafter.

BRIEF DESCRIPTION OF THE SEVERAL VIEWS OF THE DRAWINGS

Corresponding reference characters indicate corresponding parts throughout the drawings.

DETAILED DESCRIPTION

In general, the present disclosure relates to systems and methods for environmental sampling and analysis. The systems and methods advantageously provide for concurrent or simultaneous sampling of subsurface materials and sensing of one or more subsurface environmental conditions. The systems and methods are especially suited to achieve high resolution environmental site characterization where a greater amount subsurface information is obtained as compared to conventional subsurface investigations. In turn, high resolution environmental site characterization can decrease overall project costs and increase the ability to collect vital subsurface data, particularly when remediation proves necessary.

A wide range of subsurface materials can be sampled and analyzed with the method and system of the present disclosure. For example, subsurface materials include, but are not limited to, soil; groundwater; rock; various fill materials such as brick, wood, asphalt, and concrete; and waste materials such as those found in a landfill; and fluids such as groundwater. Subsurface materials can be highly heterogeneous comprising a combination of materials. Subsurface materials may contain one or more contaminants including various organic compounds such as fossil fuel derived hydrocarbon compounds (e.g., benzene, toluene, xylenes, polycyclic aromatic hydrocarbon, etc.); chlorinated compounds (e.g., trichloroethylene, tetrachloroethylene, vinyl chloride, etc.); polychlorinated biphenyls; polyfluorinated compounds (e.g., perfluorooctanesulfonic acid and perfluorooctanesulfonate); dioxins, metals (particularly, heavy metals such as lead, cadmium, chromium, etc.); and radioactive materials.

As noted, aspects of the present disclosure relate to environmental sampling and analysis systems. In various embodiments, the system comprises an outer housing; an inner housing at least partially disposed in the outer housing, the inner housing defining an interior sized and shaped to receive a sample collection liner configured to receive a sample of a subsurface material, the inner and outer housings configured to be driven into a subsurface to obtain the sample of the subsurface material; a passageway defined by at least one of the outer housing or the inner housing; and at least one of the following: a sensor supported by the outer housing, the sensor configured to detect at least one condition of the subsurface located outside of the inner and outer housings when the inner and outer housings are driven into the subsurface and a sample of a subsurface material is collected; and a fluid port positioned in the outer housing, the sampling port configured to permit the withdrawal of a subsurface fluid and/or injection of a fluid to the subsurface when the inner and outer housings are driven into the subsurface.

Figure 1:
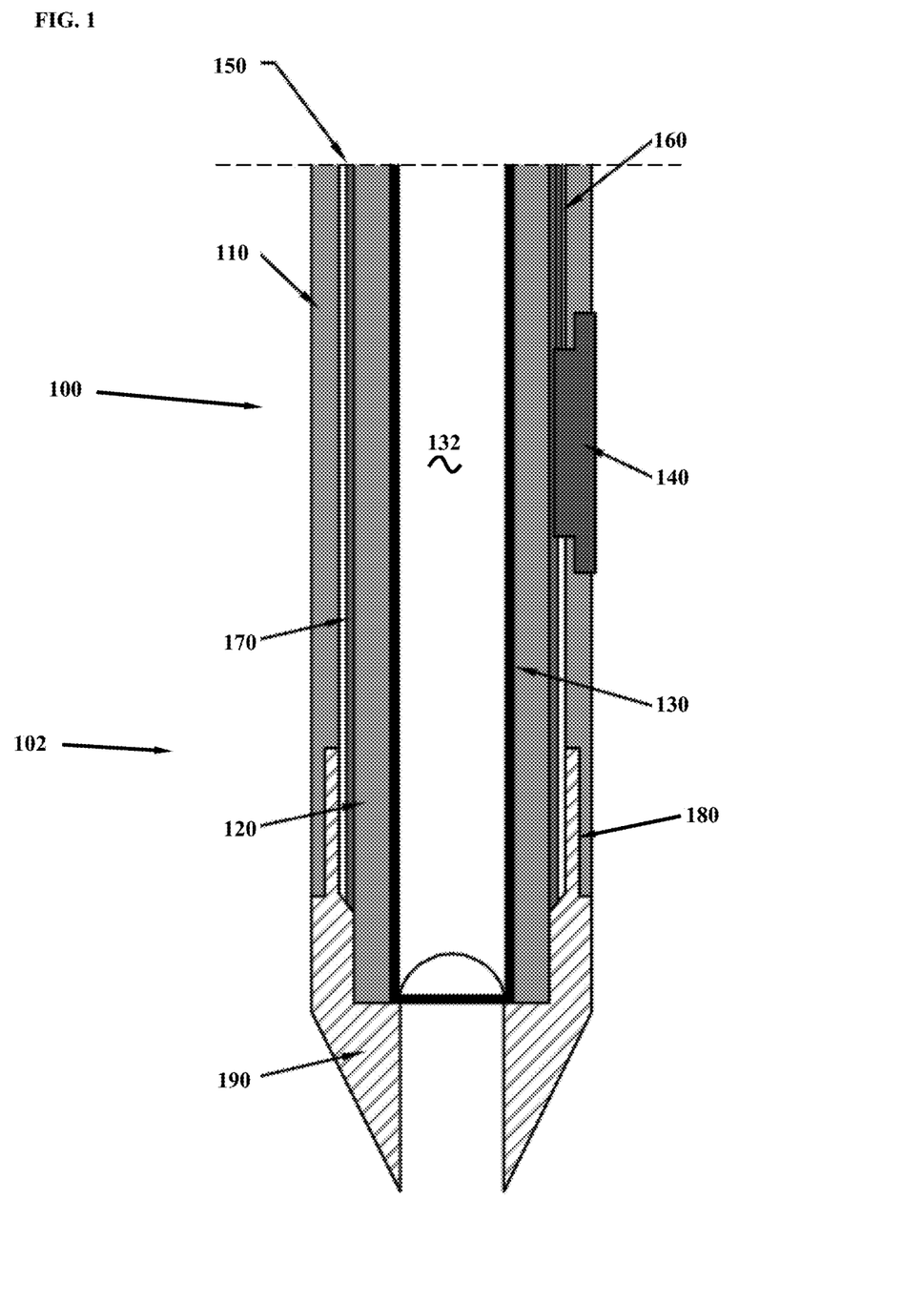
FIG. 1 is a cross-sectional view an environmental sampling and analysis system featuring a sensor according to one embodiment of the present disclosure.
Figure 2:
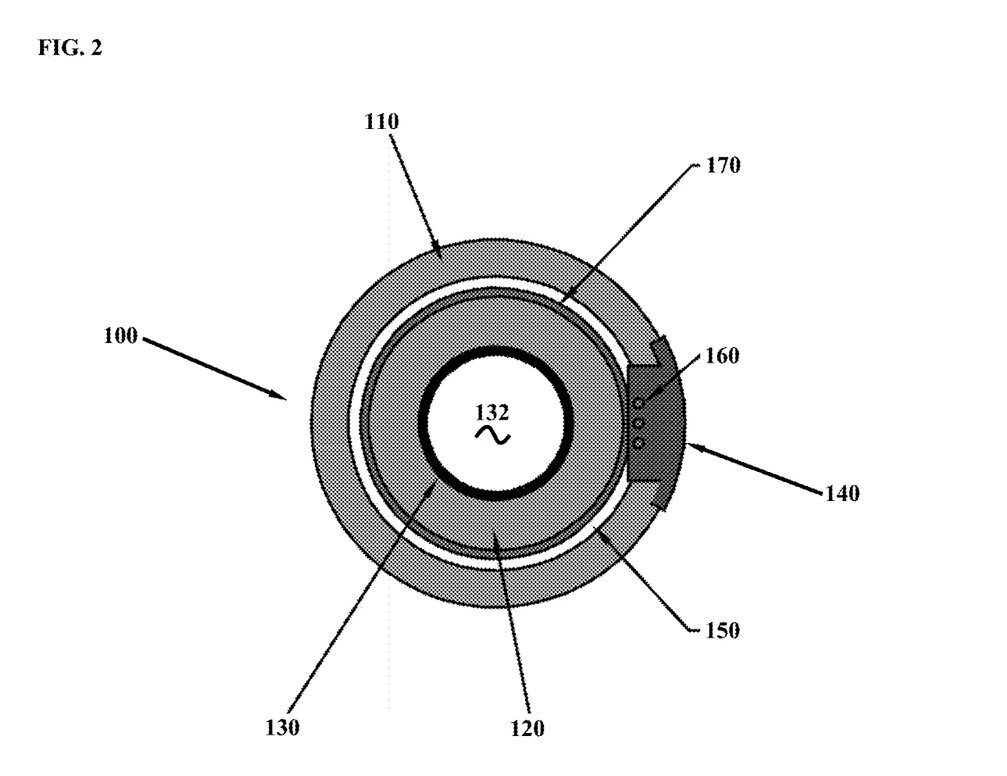
FIG. 2 is another cross-sectional view of the environmental sampling and analysis system of FIG. 1.
Figure 3:
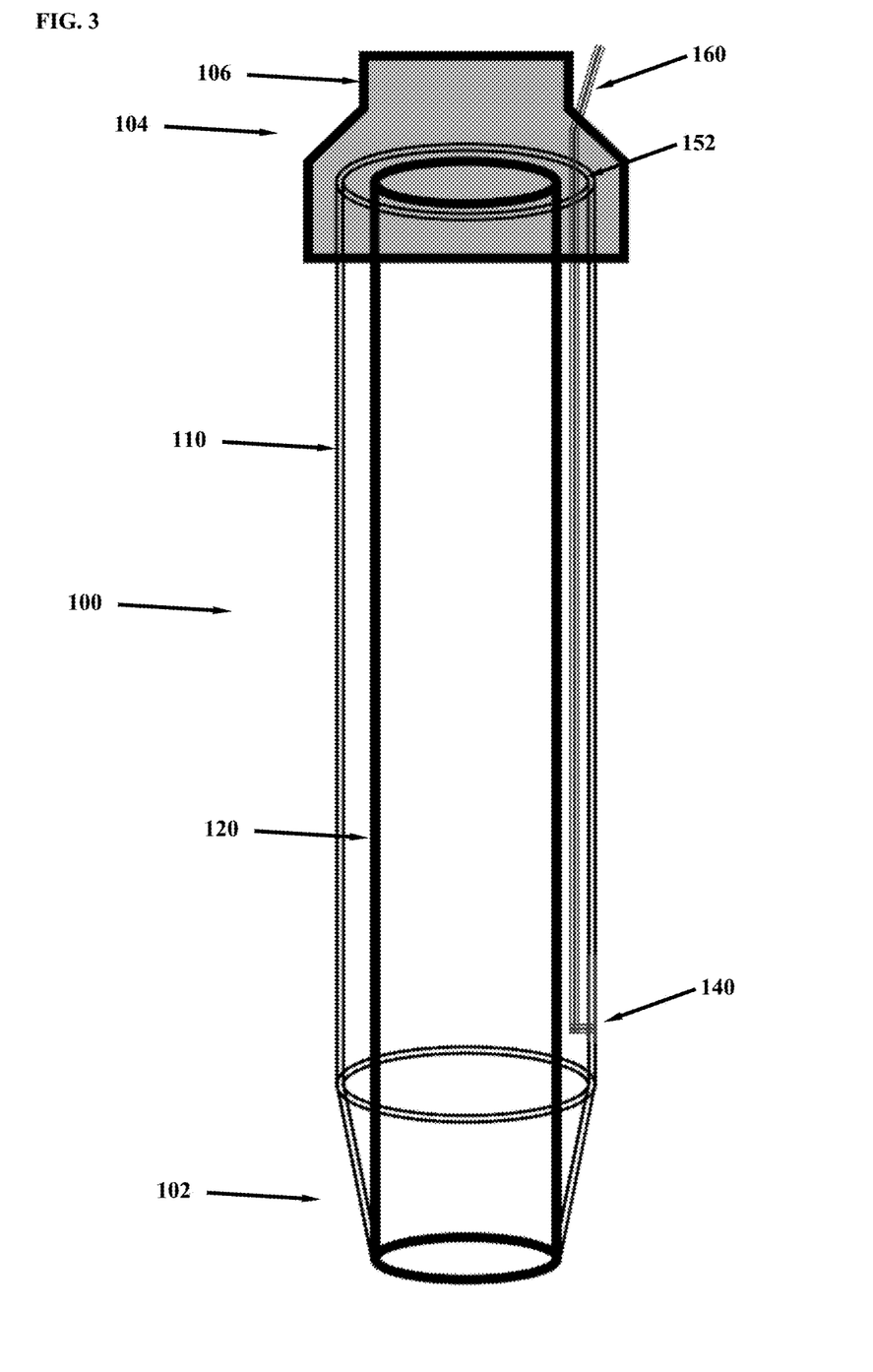
FIG. 3 is a schematic elevation view of the environmental sampling and analysis system of FIG. 1, with portions shown transparent to show interior details.
Figure 4:
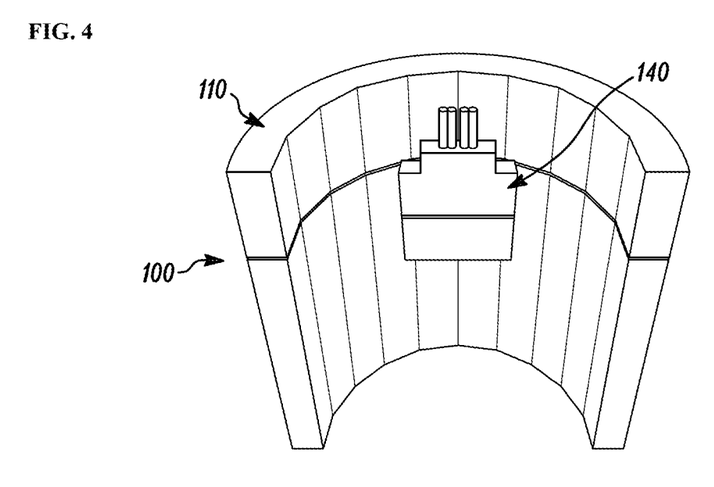
FIG. 4 is an interior cut away side view showing the outer housing and the sensor of the environmental sampling and analysis system of FIG. 1.

Referring to 1-6, one embodiment of an environmental sampling and analysis system ("system") is generally indicated at reference numeral 100. The system 100 comprises an outer housing 110 and an inner housing 120 at least partially disposed in outer housing. In one embodiment, the inner housing 120 is fully disposed in the outer housing 110. The outer and inner housings 110, 120 are constructed of a rigid material, such as metal such as steel (e.g., stainless steel). The outer and inner housings 110, 120 effectively form a sample collection device. The outer and inner housings 110, 120 (e.g., the sample collection device) are configured to be driven into the subsurface 240 (FIG. 6) in order to collect a sampling of subsurface materials (e.g., soil and/or groundwater) and/or to sense of one or more subsurface environmental conditions. The outer housing 110 defines an interior (e.g., an interior space) in which the inner housing 120 is disposed (broadly, at least partially disposed). The inner housing 120 defines an interior (e.g., an interior space) that is sized and shaped to receive a sample collection liner 130 configured to receive a sample of the subsurface material 240. The sample collection liner 130 defines a sample collection space 132 which receives and collects the sample of subsurface materials (e.g., a core sample) as the sample collection device is driven into the subsurface 240. The length of the inner and outer housings 110, 120 can be sufficiently long (e.g., 8+ feet) to provide a core of subsurface material within the inner casing that is at least 1-5 feet (e.g., about 3-5 feet) at a desired depth. Accordingly, the system 100 is generally elongate with a driven end portion 102 and a driving end portion 104 (FIG. 3). In this embodiment, the inner and outer housings 120, 110 generally extend between the driven end portion 102 and the driving end portion 104. The sample collection liner 130 may also generally extend between the driven end portion 102 and the driving end portion 104 or only a portion thereof. The system 100 may include a drive cap 106 at the driving end portion 104. The drive cap 106 is configured to be engaged by a tool, such as a direct push rig 200 (FIG. 6), to drive the system 100 into the subsurface 240. The drive cap 106 mounts on the driving end of the outer housing 110 and/or the drive end of the inner housing 120. The drive cap 106 may generally close the open upper end of outer and inner housings 110, 120.

The outer housing 110 and the inner housing 120 are generally elongate. In the illustrated embodiment, the outer housing 110 comprises a generally cylindrical wall or tube and the inner housing 120 comprises a cylindrical wall or tube. The outer housing 110 has a driving end (upper portion), generally at the driving end portion 104, and a driven end (lower portion), generally at the driven end portion 102. Likewise, the inner housing 120 has a driving end (upper portion), generally at the driving end portion 104, and a driven end (lower portion), generally at the driven end portion 102. The corresponding driving and driven ends of the outer and inner housings 110, 120 may be generally coplanar with one another or slightly offset from one another. The inner and outer housings 120, 110 may each comprise a plurality of housing segments that can be connected together (e.g., threaded together) to configure the housings (broadly, the system 100) to the desired length, corresponding to a desired depth of the sample from the subsurface 240.

The system 100 defines a sample collection opening at the driven end portion 102 (e.g., at the driven end of the system) for receiving the subsurface sample. The sample collection opening is in fluid communication with (e.g., aligned with) the sample collection space 132 such that subsurface materials that pass through the sample collection opening move into the sample collection space. The system 100 can further includes a cutting shoe 190 defining the driven end of the system. The cutting shoe 190 is configured to be driven into the subsurface 240. The cutting shoe 190 defines the sample collection opening. The cutting shoe 190 is releasably coupled to the outer housing 110 and/or the inner housing 120 (at the driven end(s) thereof). In the illustrated embodiment, the outer housing 110 of system 100 includes threads 180 for threadably coupling the cutting shoe 190 to the outer housing. Additionally or alternatively, the inner housing 120 further comprises threads 185 (FIG. 7) for threadably coupling the cutting shoe 190 to the inner housing. In some embodiments, the system 100 further comprising a cutting shoe 190 that is releasably coupled to at least one of the outer housing 110 or the inner housing 120. The outer and inner housings 110, 120 may be secured (e.g., fixed) together such that they move together as the system 100 is driven into the subsurface 240. Preferably, the cutting shoe 190 (via the threads) joins and secures the outer and inner housings 110, 120 together. In other words, the cutting shoe 190 may releasably secure the outer and inner housings 110, 120 together. Other ways of securing, such as welding, fasteners, etc., the outer and inner housings together are within the scope of the present disclosure.

In one embodiment, the system 100 may omit the sample collection liner 130. In this embodiment, the interior space of the inner housing 120 receives and collects the sample of a subsurface material (i.e., the interior space is sized and shaped to receive the sample of subsurface material). Although, in practice, use of a liner increases sample collection efficiency and avoids the potential for sample cross-contamination. In some embodiments, the system 100 is supplied with sample collection liner 130. Disposable sample collection liners are known in the art and are typically constructed of a thin plastic material that can be cut open once removed from the inner housing. The sample collection liner 130 may be at least partially transparent to permit viewing of the subsurface material collected.

Figure 5:
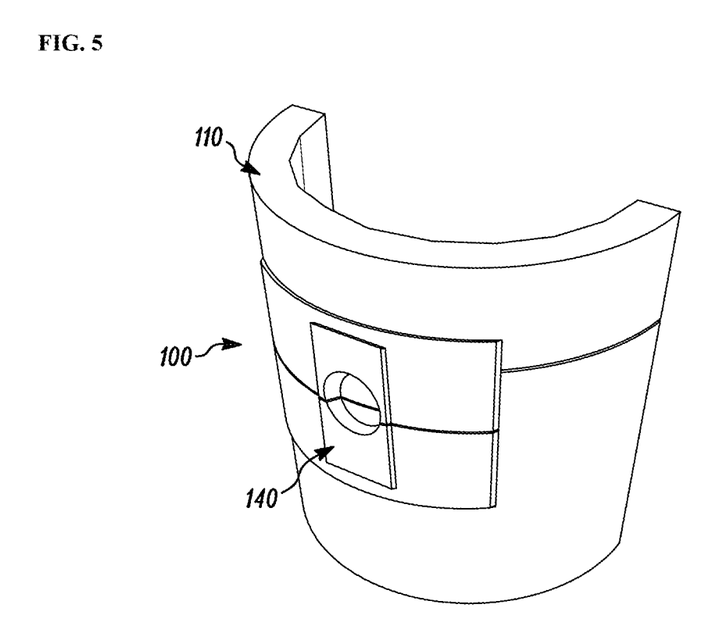
FIG. 5 is an exterior cut away side view showing the outer housing and the sensor of the exemplary environmental sampling and analysis system of FIG. 1.

The system 100 may include a sensor 140 for sensing or detecting subsurface conditions of the subsurface 240. The sensor 140 is arranged to detect a subsurface condition of the subsurface material exterior to the outer housing 110 (broadly, a condition of the subsurface 240 the system 100 is driven into). The sensor 140 is supported by the outer housing 110 and, on the illustrated embodiment, is mounted onto the outer housing. Preferably, the sensor 140 (e.g., an exterior or outer surface thereof) is generally flush with an exterior surface of the outer housing 110 (FIGS. 1 and 5). This avoids or limits the stress or drag experienced by the sensor 140 as the system 100 is driven into the subsurface 240. The sensor 140 is disposed between the driving end and driven end of the outer housing 110. Preferably, the sensor 140 is disposed at or adjacent to the driven end portion 102. In the illustrated embodiment, sensor 140 is disposed adjacent or proximate to the driven end of the outer housing 110.

The sensor 140 is configured to detect at least one condition of the subsurface 240 located outside of the inner and outer housings 120, 110 when the inner and outer housings are driven into the subsurface and a sample of a subsurface material is collected. Preferably, the sensor 140 is configured to detect a subsurface condition of a subsurface material exterior to the outer housing 110. The sensor 140 can be configured to detect at least one condition comprising one or more of a soil characteristic, a groundwater characteristic, a geotechnical characteristic, a subsurface contaminant, an organic compound, a volatile organic compound, a metal, a heavy metal, and nuclear radiation. Specific examples of sensors include a membrane interface probe, an electrical conductivity probe, an imaging probe, an optical probe, an ultra-violet optical screening tool, a fluorescence sensor, and a hydraulic profiling tool. A combination of two or more sensors can be included in the system. Other types of sensors are within the scope of the present disclosure.

The sensor 140 can be configured to detect at least one condition continuously or intermittently as the environmental sampling and analysis system is driven into the subsurface 240. For example, in some embodiments, the sensor 140 is configured to detect a condition at the same time as the environmental sampling and analysis system 100 is driven downward into the subsurface 240 (i.e., moving). In further embodiments, the sensor 140 is configured to detect a condition after the environmental sampling and analysis system 100 is driven downward into the subsurface 240 but not moving (i.e., paused). In preferred embodiments, the sample of the subsurface material is collected simultaneously with the detection of the at least one condition of the subsurface 240.

A passageway (or annulus) 150 is defined by at least one of outer housing 110 or the inner housing 120. In the illustrated embodiment, the passageway 150 comprises a circumferential gap between the cylindrical walls of the inner and outer housings 120, 110. In other embodiments, the passageway may be defined by just the outer housing 110 or the inner housing 120. The passageway 150 extends from the sensor 140 toward (e.g., to) the driving end portion 104 of the system 100. The passageway 150 may be sized and shaped to accommodate at least a portion of sensor 140 and/or one or more communication cables 160 (e.g., electrical wires). As such, the system 100 can further comprise one or more communication cables 160 communicatively coupled or communicatively/releasably coupled to the sensor 140. The one or more communication cables 160 are configured to transmit signals related to the detected condition, such as to a user interface 220 (FIG. 6) of the system 100. The one or more communication cables 160 are disposed in (e.g., extends in) the passageway 150. The system 100 defines a passageway outlet 152 in fluid communication with the passageway 150. The one or more communication cables 160 extend out of the passageway 150 through the passageway outlet 152. The passageway outlet 152 may be defined by at least one of outer housing 110 or the inner housing 120. Preferably, the passageway outlet 152 is adjacent to or at the driving end portion 104 of the system 100. In one embodiment, the drive cap 106 defines an opening at aligns with the passageway outlet 152 to permit the one or more communication cables 160 to extend through the drive cap.

Figure 6:
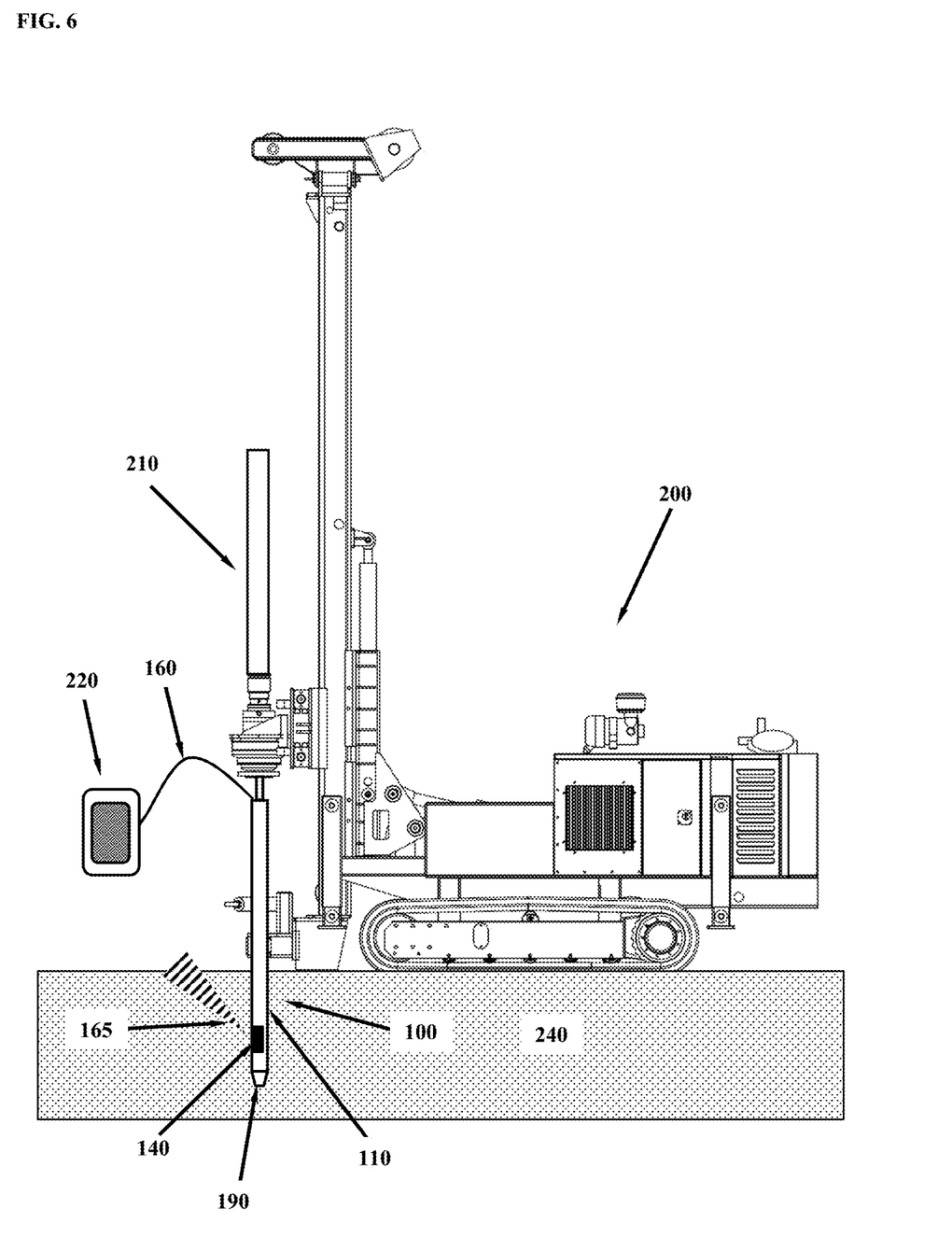
FIG. 6 is an elevation view of a direct push rig with the exemplary environmental sampling and analysis system featuring the sensor.

In other embodiments, instead of or in addition to the one or more communication cables 160, the system 100 can include a wireless communication device 165 (FIG. 6). The wireless communication device 165 is configured to transmit signals related to the detected condition, such as to the user interface 220 of the system. The wireless communication device 165 may be communicatively coupled to the sensor 140 or part of the sensor. The wireless communication device 165 can be at least partially positioned in the passageway 150 and/or supported by the outer housing 110. The wireless communication device 165 can comprise at least one selected from the group consisting of a Wi-Fi device, a Bluetooth device, and a RF device, although other suitable wireless communication devices are within the scope of the present disclosure.

In some embodiments, the system 100 may include insulation 170 (e.g., an insulation material) disposed in the passageway 150. The insulation 170 can minimize any significant heat transfer to the inner housing 120, sample collection liner 130, and subsurface material collected therein during the driving of the sample collection device, which could negatively affect or bias sampling data from the subsurface material (e.g., soil/groundwater) collected. In some embodiments, the insulation 170 comprises a silica aerogel, although other suitable materials are within the scope of the present disclosure. The system 100 can also include a heat resistant material or additional insulation in the passageway 150 around the sensor 140 to protect the sensor from vibration and stress.

As mentioned above, the system 100 can include a user interface 220. The user interface 220 communicatively couples to the sensor 140, via the communication cables 160 and/or the wireless communication device 165, to receive the signals related to the detected condition. In other words, the signals transmitted from the communication cables 160 and/or wireless communication device 165 can be received by the user interface 220. The user interface 220 includes a display, such as a touch screen, for displaying the detected condition to an operator. The user interface 220 may include a memory (e.g., non-tangible storage medium) for storing the detected condition. The user interface 220 may comprise a computing device such as a smart phone, a tablet computer, a laptop or any other suitable device.

The system 100 may include a center rod (not shown) that is inserted into the interior space of the inner housing 120 to close the sample collection opening while the system is being driven into the subsurface 240 to a start or initial depth. This prevent the system 100 from receiving and collecting a sample of the subsurface material until the driving end portion 102 of the system 100 reaches the start depth of where the sample is to be taken. The center rod is inserted through the open top of the outer and inner housings 120, 110. Once the driving end portion 102 is at the start depth where the sample is to start, the operator can remove (e.g., lift) the center rod out of the interior space of the inner housing 120 (though the open top thereof) to open sample collection opening. In some embodiments, the operator may then insert the sample collection liner 130 into the interior space of the inner housing 120 (through the open top thereof) after the center rod is removed. After the center rod is removed, the system 100 can continue to be driven into the subsurface 240 to the target or desired depth (e.g., the deepest point in the subsurface 240 for the sample). Because the sample collection opening is now open (e.g., no longer closed by the center rod), as the system 100 is driven into the subsurface 240 toward the target depth, the sample collection liner 130 receives and collects the sample of subsurface materials. In one embodiment, after the system 100 reaches the target depth, the sample collection liner 130 with the sample is then removed (e.g., lifted) from the inner housing 120, while the inner and outer housings 120, 110 remain in the subsurface 240. In other embodiments, the sample collection liner 130 may be removed after the system 100 (e.g., inner and outer housings 120, 110) are removed (e.g., lifted) from the subsurface 240. The sensor 140 may detect the condition of the subsurface 240 at generally anytime, such as when the system 100 is being driven into the subsurface, once the subsurface has reached the start depth or target depth, or while the system 100 is being removed from the subsurface.

Referring to FIG. 6, the environmental sampling and analysis system 100 can be used with a direct push rig 200. The direct push rig 200 drives the system 100 into the subsurface 240. For example, the system 100 can be hydraulically driven into the subsurface 240 by a hydraulic hammer 210 of the direct push rig 200. Other systems and methods of driving the system 100 into the subsurface 240 are within the scope of the present disclosure.

Figure 7:
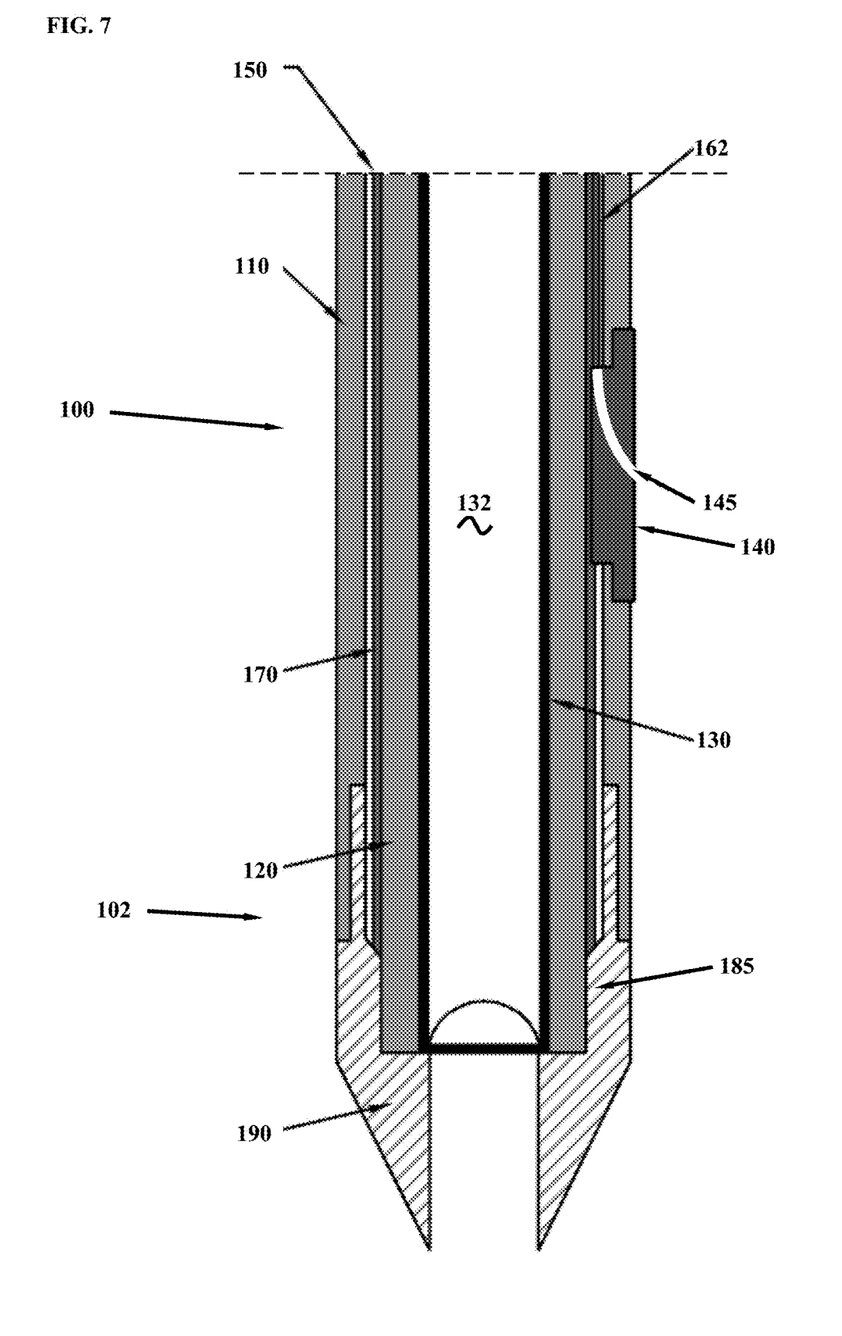
FIG. 7 is a cross-sectional view of an exemplary environmental sampling and analysis system featuring a fluid port according to another embodiment of the present disclosure.
Figure 8:
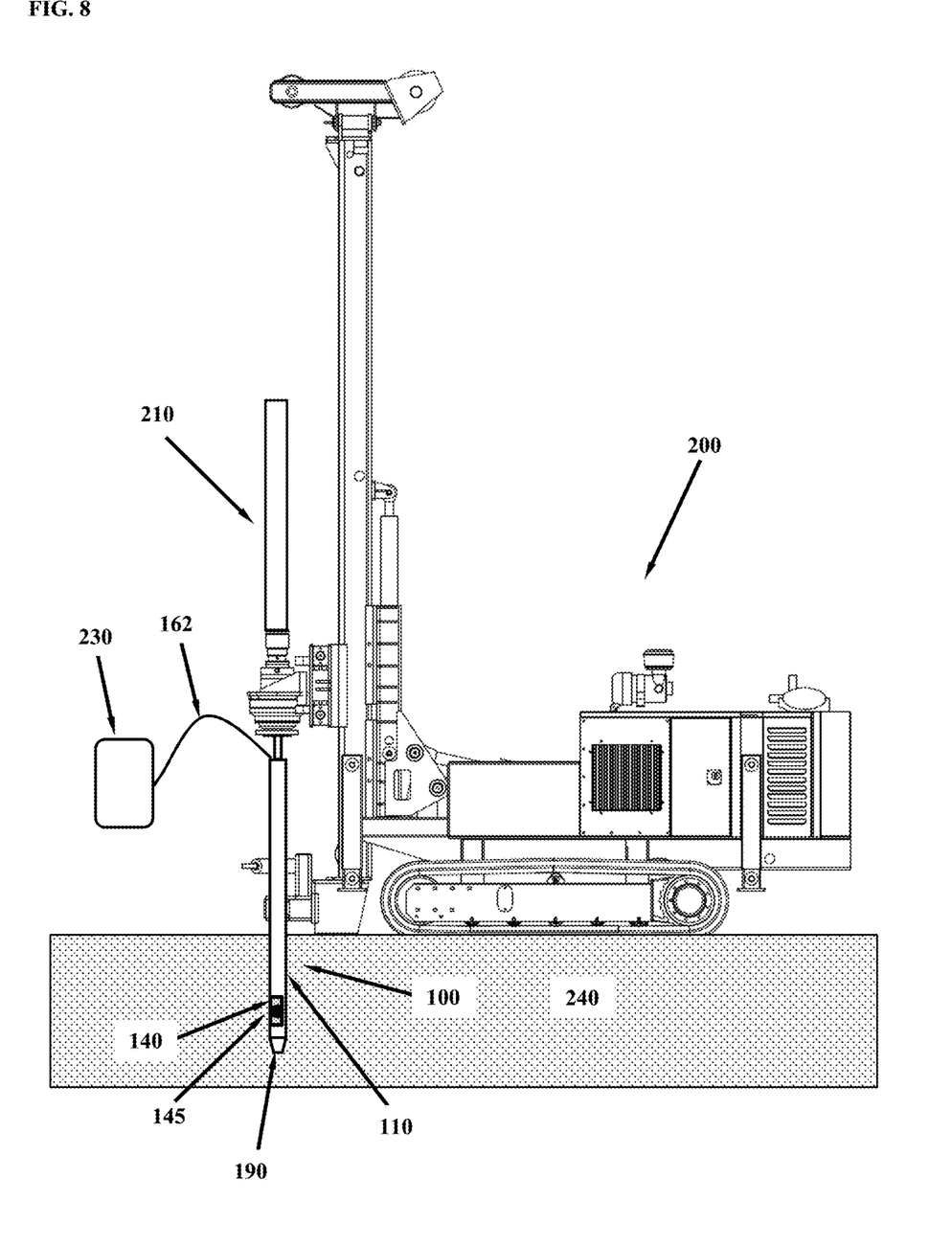
FIG. 8 is an elevation view of the direct push rig with the environmental sampling and analysis system of FIG. 7.

Referring to FIGS. 7 and 8, another embodiment of an environmental sampling and analysis system is generally shown. The system shown in FIGS. 7 and 8 is generally analogous to the system shown in FIGS. 1-6 and, thus, for ease of comprehension, identical reference numerals are used. Accordingly, unless clearly stated or indicated otherwise, the above descriptions regarding the system shown in FIGS. 1-6 also apply to the system shown in FIGS. 7 and 8.

In this embodiment, the system 100 includes a fluid port 145. The fluid port 145 is configured to permit the withdrawal of a subsurface fluid and/or injection of a fluid to the subsurface when the inner and outer housings 120, 110 are driven into the subsurface 240. The fluid port 145 is supported by (e.g., positioned in) the outer housing 110. In the illustrated embodiment, the fluid port 145 is integrated with the sensor 140. In other embodiments, the fluid port 145 may be spaced apart from the sensor 140. Broadly, the system 100 can include at least one of the sensor 140 and the fluid port 145. Preferably, the system 100 includes both the sensor 140 and the fluid port 145.

The fluid port 145 is configured to permit fluid to flow therethrough when the inner and outer housings 120, 110 are driven into the subsurface 240. In this embodiment, the system 100 includes a conduit 162 (e.g., a fluid conduit) that defines a lumen in fluid communication with fluid port 145. The conduit is configured to convey fluid to or from fluid port 145. The conduit 162 is disposed in (e.g., extends in) the passageway 150. The conduit 162 extends out of the passageway 150 through the passageway outlet 152. The conduit 162 may also extend through the opening in the drive cap 106. The conduit 162 is configured to be operatively connected to a pump and/or pressurized fluid container 230 for moving a fluid in the lumen of conduit (FIG. 7). For example, the conduit 162 can include a fitting to fluidly couple the conduit to the pressurized fluid container 230. The fluid port 145 can be used to withdraw fluid from the subsurface 240, such as groundwater or soil gas. Any withdrawn fluid can be subsequently fed to a field analysis device (e.g., PID) or collected in suitable containers for preservation and/or further analysis. In addition, the fluid port 145 can be used to inject a fluid into the subsurface 240, such as a fluid for remediating soil (e.g., oxidants or steam). In one embodiment, the fluid port 145 may be used to inject a fluid into the subsurface 240 and then used to withdraw the injected fluid.

Figure 9:
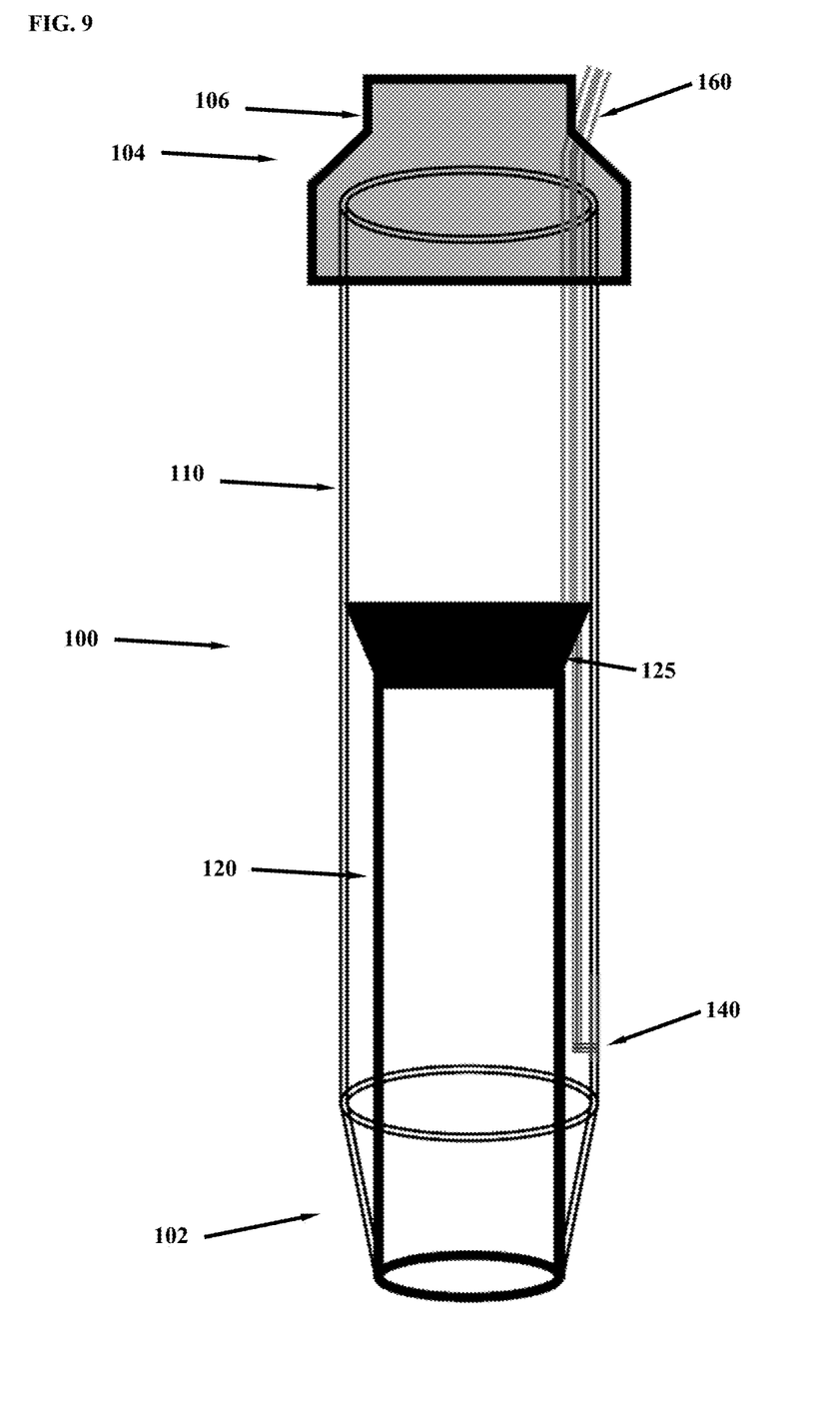
FIG. 9 is a schematic elevation view of an environmental sampling and analysis system according to another embodiment of the present disclosure.

Referring to FIG. 9, another embodiment of an environmental sampling and analysis system is generally shown. The system shown in FIG. 9 is generally analogous to the systems shown in FIGS. 1-8 and, thus, for ease of comprehension, identical reference numerals are used. Accordingly, unless clearly stated or indicated otherwise, the above descriptions regarding the systems shown in FIGS. 1-8 also apply to the system shown in FIG. 9.

In this embodiment, the inner housing 120 only extends partially along the length of the outer housing 110, such as about half the length although other lengths (e.g., about ⅙, about ⅕, about ¼, about ⅓, about ⅔) are within the scope of the present disclosure. The inner housing 120 generally extends from the driven end portion 102 toward the driving end portion 104 of the system 100. The upper or driving end of the inner housing 120 is spaced from the driving end of the outer housing 110. In particular, the upper or driving end of the inner housing 120 is disposed between the driven and driving ends of the outer housing. Accordingly, this system 100 may use a shorter sample collection liner 130 than the systems shown in FIGS. 1-8. The interior space of the inner housing 120 is in fluid communication with an interior space of the outer housing 110 (in the embodiments shown in FIGS. 1-8, the inner housing is disposed in the interior space of the outer housing). Specifically, the interior space of the inner housing 120 has an open upper end in communication with the interior space of the outer housing. The system 100 includes a liner guide or funnel 125 adjacent (e.g., at) the upper end of the inner housing 120. The liner guide 125 guides the sample collection liner 130 into the interior space of the inner housing 120 when the sample collection liner is inserted downward into the outer housing 110 from the open upper end thereof (e.g., along the interior space of the outer housing). This embodiment, eliminates the need to have the inner housing 120 extend the entire length of the outer housing 110, saving material costs and reducing the amount of time need to take a sample. Generally, the inner and outer housings 120, 110 come in sections (e.g., 4-ft sections) that are threaded together in an end-to-end relationship to configure the system 100 to have a sufficient length to reach a desired depth (e.g., 16 ft). By only having the inner housing 120 extend part of the way along the length of the system 100, an operator does not need to keep adding inner housing sections every time an outer housing section is added, making it faster and easier to configure the system 100 to the desired length. For example, the lower-most section of the system 100 may include both the outer and inner housings 110, 120 (along with the cutting shoe 190) while each additional section of the system only includes the outer housing.

Further aspects of the present disclosure relate to a method for environmental sampling and analysis using the systems 100 described herein. In various embodiments, the method comprises driving the system 100 into the subsurface 240, collecting a sample of a subsurface material in the system as the system is driven into the subsurface, and detecting at least one condition of the subsurface with the sensor 140 in the system. In one embodiment, the system 100 is hydraulically driven into the subsurface 240 (e.g., via a hydraulic hammer (210) of a direct push rig (200)) (FIGS. 6 and 8).

In this method, the at least one condition can be detected continuously or intermittently as the system 100 is driven into the subsurface 240. For example, in some embodiments, the condition is detected at the same time as the system is driven downward into the subsurface (i.e., moving). In this embodiment, the user interface 220 may direct the sensor 140 to take readings at set intervals (e.g., time intervals, depth intervals). In further embodiments, the condition is detected after the system 100 is driven downward into the subsurface but not moving (i.e., paused). In preferred embodiments, the sample of the subsurface material is collected simultaneously with the detection of the at least one condition of the subsurface 240.

The subsurface condition that is detected can comprises one or more of a soil characteristic, a groundwater characteristic, a geotechnical characteristic, a subsurface contaminant, an organic compound, a volatile organic compound, a metal, a heavy metal, and nuclear radiation. Specific examples of conditions that can be detected include, but are not limited to, one or more of relative volatile organic compounds (VOC) concentration, conductivity, polycyclic aromatic hydrocarbon fluorescence, and physical or geotechnical soil characteristics.

The method can further comprise transmitting the at least one condition to the user interface 220. For example, at least one condition can be transmitted over a wired (via the communication cables 160) and/or wireless connection (via the wireless communication device 165) to the user interface 220. The method can also include logging at least one condition with the user interface 220, with the logged conditions stored in the memory.

The method can further comprise withdrawing a subsurface fluid and/or injecting a fluid into the subsurface 240. Fluids such as groundwater or soil gas can be withdrawn through the environmental sampling and analysis system 100. For example, the fluids can be withdrawn after the system reaches the target depth and/or at any depth. For example, the fluids can be withdrawn at set intervals (e.g., time intervals, depth intervals) as the system 100 is being driven into the subsurface 240. Any withdrawn fluid can be subsequently fed to a field analysis device (e.g., photoionization detector) or collected in suitable containers for preservation and/or further analysis. Fluids such as those for remediating soil/groundwater (e.g., oxidants or steam) can also be injected into the subsurface through the environmental sampling and analysis system. For example, the fluids can be injected after the system reaches the target depth and/or at any depth. For example, the fluids can be injected at set intervals (e.g., time intervals, depth intervals) as the system 100 is being driven into the subsurface 240.

The method can include various combinations of these steps. For example, the method can include detecting at least one condition (via the sensor 140) and injecting a fluid into the subsurface 240. Detecting the condition with the sensor 140 can occur simultaneously with the injecting of the fluid. In another example, the method can include detecting at least one condition (via the sensor 140) and withdrawing a fluid from the subsurface 240 for further analysis. Detecting the condition with the sensor 140 can occur simultaneously with the withdrawing of the fluid. It is understood the method may include other steps or operations, including steps consistent with the descriptions herein.

The order of execution or performance of the steps or operations in embodiments of the aspects of the disclosure illustrated and described herein is not essential, unless otherwise specified. That is, the operations may be performed in any order, unless otherwise specified, and embodiments of the aspects of the disclosure may include additional or fewer operations than those disclosed herein. For example, it is contemplated that executing or performing a particular operation before, contemporaneously with, or after another operation is within the scope of aspects of the disclosure.

Having described the disclosure in detail, it will be apparent that modifications and variations are possible without departing from the scope of the disclosure defined in the appended claims.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained. As various changes could be made in the above systems and methods without departing from the scope of the disclosure, it is intended that all matter contained in the above description and shown in the accompanying drawings shall be interpreted as illustrative and not in a limiting sense.

The invention claimed is:

1. An environmental sampling and analysis system comprising:
    an outer housing having an interior;
    an inner housing at least partially disposed in the interior of the outer housing, the inner housing having an interior sized and shaped to receive a sample collection liner configured to receive a sample of a subsurface material, the inner and outer housings configured to be driven into a subsurface to obtain the sample of the subsurface material;
    a passageway defined by at least one of the outer housing or the inner housing; and
    at least one of the following:
        a sensor supported by the outer housing, the sensor arranged to detect at least one condition of the subsurface located outside of the outer housing when the inner and outer housings are driven into the subsurface and the sample of a subsurface material is collected; or
        a fluid port positioned in the outer housing, the fluid port arranged to permit the withdrawal of a subsurface fluid and/or injection of a fluid to the subsurface when the inner and outer housings are driven into the subsurface.

2. The system of claim 1, wherein the system comprises the sensor supported by the outer housing and arranged to detect the at least one condition of the subsurface located outside of the outer housing when the inner and outer housings are driven into the subsurface and the sample of a subsurface material is collected.

3. The system of claim 2, further comprising one or more communication cables communicatively coupled to the sensor and configured to transmit signals related to the detected condition, the one or more communication cables extending in the passageway.

4. The system of claim 3, further comprising a passageway outlet in fluid communication with the passageway, wherein the communication cables extend out of the passageway through the passageway outlet.

5. The system of claim 2, wherein the sensor comprises one or more of a membrane interface probe, an electrical conductivity probe, an imaging probe, an optical probe, an ultra-violet optical screening tool, a fluorescence sensor, and a hydraulic profiling tool.

6. The system of claim 2, wherein the sensor is mounted to the outer housing.

7. The system of claim 6, wherein the sensor is generally flush with an exterior surface of the outer housing.

8. The system of claim 2, wherein the outer housing has a driving end and a driven end, and the sensor is disposed between the driving end and driven end.

9. The system of claim 8, wherein the sensor is disposed proximate to the driven end.

10. The system of claim 2, wherein the sensor is arranged to detect a subsurface condition of a subsurface material exterior to the outer housing.

11. The system of claim 2, further comprising a wireless communication device configured to transmit signals related to the detected condition.

12. The system of claim 11, wherein the wireless communication device is at least partially positioned in the passageway and/or supported by the outer housing.

13. The system of claim 11, wherein the wireless communication device comprises at least one selected from the group consisting of a Wi-Fi device, a Bluetooth device, and a RF device.

14. The system of claim 1, wherein the at least one condition comprises one or more of a soil characteristic, a groundwater characteristic, a geotechnical characteristic, a subsurface contaminant, an organic compound, a volatile organic compound, a metal, a heavy metal, and nuclear radiation.

15. The system of claim 1, wherein the system comprises the fluid port positioned in the outer housing.

16. The system of claim 15, wherein the fluid port is configured to permit fluid to flow therethrough when the inner and outer housings are driven into the subsurface, the system further comprising a conduit defining a lumen in fluid communication with the fluid port the conduit extending in the passageway, the conduit configured to convey fluid to or from the fluid port.

17. The system of claim 16, wherein the conduit is configured to be operatively connected to a pump and/or pressurized fluid container for moving a fluid in the lumen of the conduit.

18. The system of claim 17, further comprising a passageway outlet in fluid communication with the passageway, wherein the conduit extends out of the passageway through the passageway outlet.

19. The system of claim 1, wherein the outer housing comprises a cylindrical wall, the inner housing comprises a cylindrical wall and the passageway comprises a circumferential gap between the cylindrical walls of the inner and outer housings.

20. The system of claim 1, further comprising a cutting shoe, wherein the outer housing comprises threads for the cutting shoe to be releasably coupled to the outer housing.

21. The system of claim 1, further comprising a cutting shoe, wherein the inner housing comprises threads for the cutting shoe to be releasably coupled to the inner housing.

22. The system of claim 1, further comprising a cutting shoe releasably coupled to at least one of the outer housing or the inner housing.

23. The system of claim 1, further comprising the sample collection liner.

24. The system of claim 1, further comprising insulation disposed in the passageway.

25. The system of claim 24, wherein the insulation comprises a silica aerogel.

26. The system of claim 1, wherein the subsurface material comprises soil and/or groundwater.

27. The system of claim 1, wherein the outer housing has a driving end and a driven end, the inner housing having a driving end and a driven end, the driving end of the inner housing being spaced apart from the driving end of the outer housing toward the driven end of the outer housing.

28. The system of claim 27, wherein the outer housing defines an interior, the interior of the outer housing in fluid communication with the interior of the inner housing.

29. The system of claim 28, further comprising a liner guide arranged to guide the sample collection liner into the interior of the inner housing from the interior of the outer housing as the sample collection liner is inserted into the interior of the inner housing.

30. The system of claim 1, wherein the interior of the inner housing is at least partially disposed in the interior of the outer housing.

31. A method for environmental sampling and analysis, the method comprising: driving an environmental sampling and analysis system comprising a sensor arranged to detect at least one condition of the subsurface located outside of the system when the system is driven into the subsurface; collecting a sample of a subsurface material in the environmental sampling and analysis system as the system is driven into the subsurface; and detecting at least one condition of the subsurface with the sensor in the environmental sampling and analysis system; wherein the environmental sampling and analysis system comprises: an outer housing having an interior; an inner housing at least partially disposed in the interior of the outer housing, the inner housing having an interior sized and shaped to receive a sample collection liner configured to receive a sample of a subsurface material, the inner and outer housings configured to be driven into a subsurface to obtain the sample of the subsurface material; and a passageway defined by at least one of the outer housing or the inner housing; wherein the sensor is supported by the outer housing.

32. The method of claim 31, wherein the at least one condition is detected continuously or intermittently as the environmental sampling and analysis system is driven into the subsurface.

33. The method of claim 31, wherein the sample of the subsurface material is collected simultaneously with the detection of the at least one condition of the subsurface.

34. The method of claim 31, wherein the environmental sampling and analysis system is hydraulically driven into the subsurface.

35. The method of claim 31, further comprising transmitting the at least one condition to a computing device.

36. The method of claim 35, wherein the at least one condition is transmitted over a wired and/or wireless connection to the computing device.

37. The method of claim 36, further comprising logging the at least one condition with the computing device, the computing device comprising memory for storing logged conditions.

38. The method of claim 31, wherein the at least one condition comprises one or more of a soil characteristic, a groundwater characteristic, a geotechnical characteristic, a subsurface contaminant, an organic compound, a volatile organic compound, a metal, a heavy metal, and nuclear radiation.

39. The method of claim 31, wherein the at least one condition comprises one or more of relative volatile organic compounds (VOC) concentration, conductivity, polycyclic aromatic hydrocarbon fluorescence, and physical or geotechnical soil characteristics.

40. The method of claim 31, further comprising withdrawing a subsurface fluid and/or injecting a fluid into the subsurface.

* * * * *